United States Patent [19]

Vandermast et al.

[11] Patent Number: 4,845,827
[45] Date of Patent: Jul. 11, 1989

[54] LUER FITTING INSTALLATION TOOL

[75] Inventors: Nueboch Vandermast, Flippin; Carl Ramey, Yellville, both of Ariz.

[73] Assignee: Ark-Plas Products, Flippin, Ark.

[21] Appl. No.: 206,020

[22] Filed: Jun. 10, 1988

[51] Int. Cl.[4] .............................................. B23P 19/02
[52] U.S. Cl. ...................................................... 29/280
[58] Field of Search ................. 29/251, 252, 275, 254, 29/278, 280, 282, 283

[56] References Cited

U.S. PATENT DOCUMENTS

| | | | |
|---|---|---|---|
| 2,641,379 | 6/1953 | Barbaro | 29/275 |
| 4,473,932 | 10/1984 | Widner | 29/251 |
| 4,538,335 | 9/1985 | Moore | 29/251 |

FOREIGN PATENT DOCUMENTS 578425  6/1946  United Kingdom ................. 29/251

*Primary Examiner*—Robert C. Watson
*Attorney, Agent, or Firm*—Stephen D. Carver

[57] ABSTRACT

Apparatus for assembling and installing Luer fittings comprises a hand held tool and an associated jig. The main body of the tool comprises an elongated, generally cylindrical housing externally configured to define a comfortable hand grip. An integral, reduced diameter nozzle projects forwardly from the housing for selectively, slidably engaging the male portion of a desired Luer fitting to be assembled. The housing concentrically mounts a spring-biased plunger driven by an external button adapted to be contacted by the user's hand. A metallic drive pin emanating from the plunger drive shaft penetrates the housing nozzle. An internal snap ring seated within an internal housing ring groove limits longitudinal plunger motion. The apparatus also includes an associated jig adapted to be mounted upon a supporting work surface. The jig firmly retains the locking ring of a Luer fitting in proper position for assembly. The male portion of the Luer fitting is slidably inserted into the nozzle and forcibly injected into engagement with the Luer lock ring by compression of the tool plunger. The female portion of the Luer fitting may then be manually screwed into the Luer lock ring to complete assembly.

12 Claims, 2 Drawing Sheets

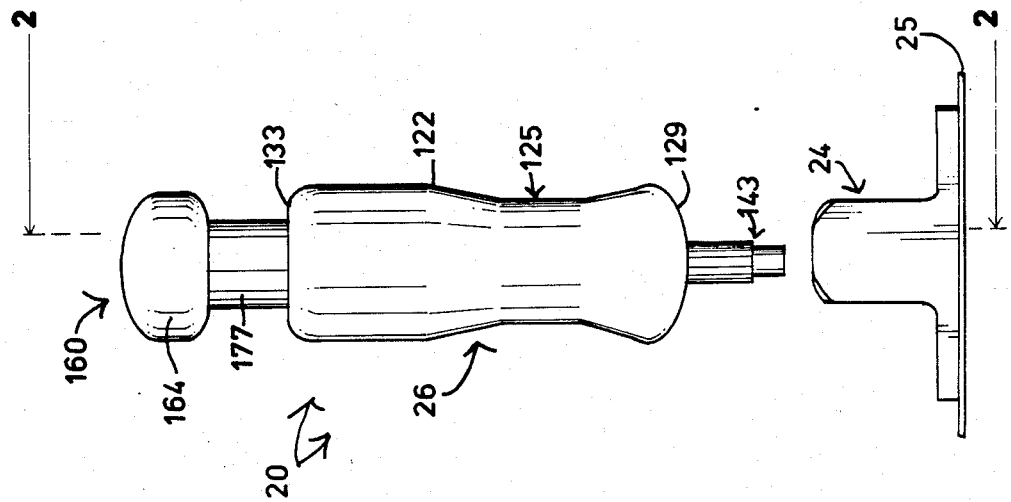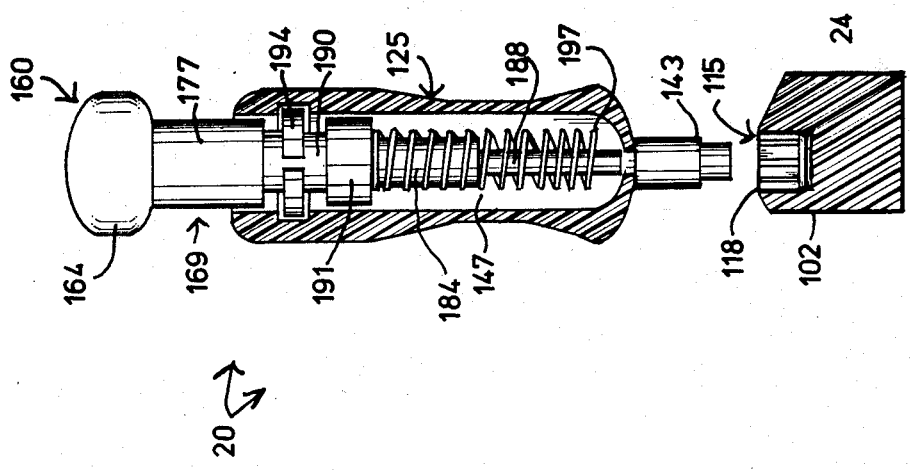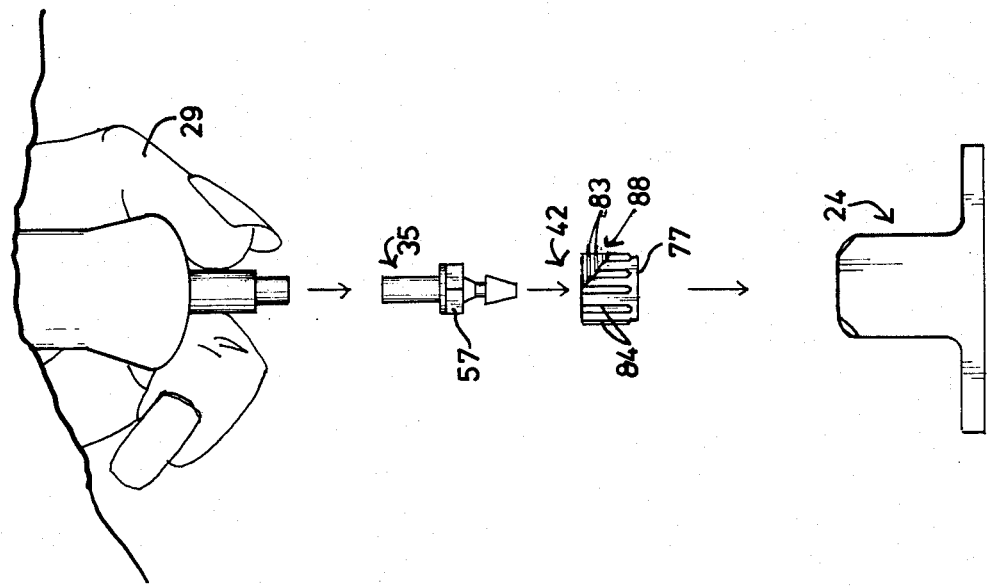

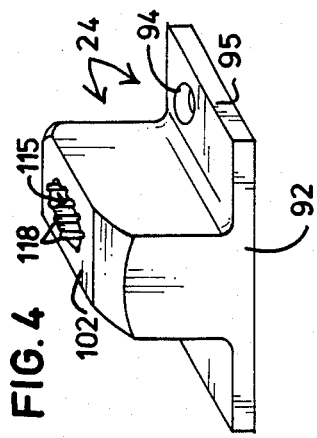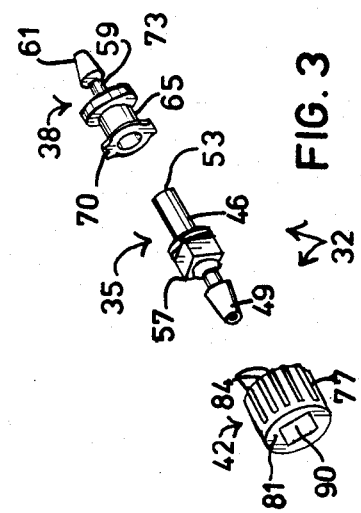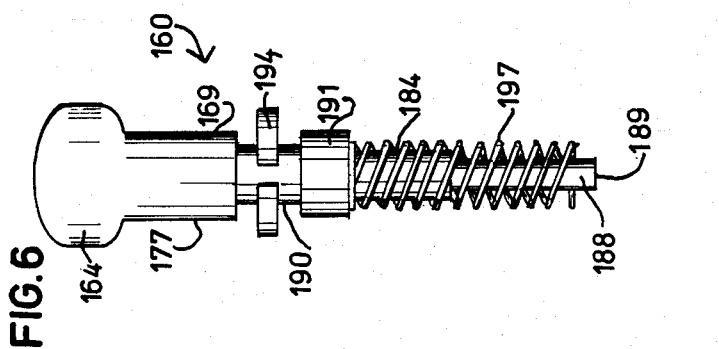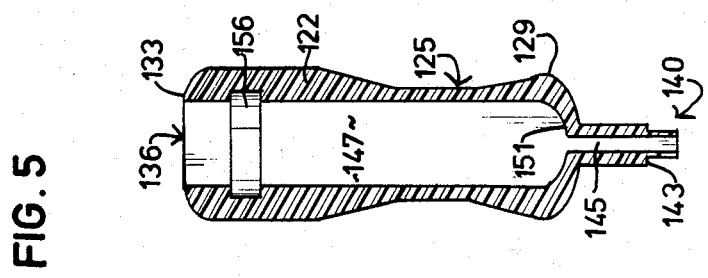

LUER FITTING INSTALLATION TOOL

BACKGROUND OF THE INVENTION

The present invention relates broadly to tools for facilitating the assembly or coupling of plastic tubing connectors. More specifically, the present invention relates to apparatus for quick-connecting Luer lock fittings.

As will be appreciated by those skilled in the art, typical Luer fittings comprise cooperating male and female portions which couple to join sections of flexible tubing. For example, the Luer lock connection device disclosed by Dennehey in U.S. Pat. No. 4,294,250 issued Oct. 13, 1981 includes interfitting male and female connectors. An outer shroud associated with the male portion of the fitting shields the junction from contamination.

U.S. Pat. No. 4,597,758, issued July 1, 1986 to Aalto et al. discloses means for sealing the male portion of the Luer fitting to prevent leakage of fluids in pressurized containers. Therein are described typical locking Luer fittings comprising a male, a female, and a locking ring portion. Similar locking Luer fittings are addressed in Parham, U.S. Pat. No. 4,566,480, issued Jan. 28, 1986.

In the prior art known to us, however, there is no teaching or suggestion provided for facilitating quick-connection of the cooperating interlocking portions. In particular, no means are disclosed for conveniently installing the locking ring. Hence it would seem desirable to provide a tool to facilitate quick assembly of the cooperating parts of typical Luer lock fittings prior to their installation on the desired surgical tubing sections.

Because the Luer lock fittings are typically very small and their cooperating parts are sometimes difficult to distinguish, manipulation of the interlocking portions can be tedious and time-consuming. Because the interlocking components are designed for precision fitting, they must be accurately positioned and retained in position during installation. Moreover, it is extremely difficult to manually apply adequate pressure to attain a sealing, interfitting connection while maintaining the various components in proper position for installation. Particularly in an environment where time is a critical factor, obtaining a satisfactory couple is extremely difficult.

As will be appreciated, a wide variety of tools and techniques for assembling other plastic parts items has been suggested in the prior art included in the broad category of installation devices. For example, U.S. Pat. No. 4,903,205, issued to Hill on Jan. 15, 1985, describes a pneumatic expansion rivet applicator which facilitates the installation of expansion rivets into a supporting surface. The device comprises an elongated piston which forcibly expels and "injects" an expansion rivet in response to pressure applied to the outer shell of the tool housing.

Another rivet driver device is disclosed in the earlier U.S. Pat. No. 3,442,112, issued May 6, 1969 to Abromavage et al. The tool comprises a cylindrical housing having an integral tubular barrel which receives a rivet to be installed. A screw-fitted removable cap is provided to limit longitudinal movement of the barrel within its cylindrical housing. Of lesser relevance is the rivet gun described by Briles, U.S. Pat. No. 3,908,257, issued Sept. 30, 1975.

However, none of the prior art known to us adequately addresses the need for a tool to facilitate the quick-connection and installation of surgical Luer lock fittings. The cited prior art does not include suggestions as to how to secure various cooperating portions of multiple-component parts during assembly and installation. Hence it would seem desirable to provide a tool to facilitate the quick connection of the cooperating parts of typical Luer lock fittings.

SUMMARY OF THE INVENTION

The present invention is directed to apparatus for facilitating the assembly of a surgical Luer fitting. More particularly, apparatus is disclosed for quick-connection of a locking ring upon a Luer fitting. Such Luer fittings are typically used to provide a sterile, pressure-tight connection between separate portions of flexible tubing such as may typically be used with pneumatics, hydraulics, surgical applications, and the like. A typical plastic Luer fitting comprises three components: an elongated male portion, a corresponding, elongated female portion, and a rigid locking ring. The locking ring is provided to securely seal the assembled connector. The apparatus of the present invention retains the male portion and the locking ring of the Luer fitting in position to facilitate their quick, sealing assembly.

The apparatus broadly comprises an elongated, cylindrical tool and a cooperative jig. The tool is preferably externally configured to fit comfortably in the user's hand. An integral, tubular nozzle preferably extends from one end of the tool to receive Luer fittings of various types and sizes commonly known in the art.

The interior of the tool is configured to receive a slidable plunger. A flexible spring biases the plunger between a tool-load and an install position. A retainer ring limits longitudinal motion of the plunger to prevent its accidental disassociation from the tool.

A rigid jig adapted to be mounted to a supporting work surface firmly retains the locking ring of the Luer fitting in position for installation.

In use, a Luer fitting locking ring is secured in position within the jig. The male portion of the Luer fitting is slidably inserted into the nozzle of the tool. The male portion is forcibly fitted into the locking ring by manual compression of the plunger. The female portion is then manually screwed into the locking ring.

Thus it is a broad object of the present invention to provide apparatus which facilitates the manual connection of the various components of a locking Luer fitting.

Another fundamental object of the present invention is to provide apparatus for securing the locking ring portion of a Luer fitting in position for installation upon cooperating male and female fitting portions.

Yet another object of the present invention is to provide apparatus which permits the user to supply adequate pressure to attain a satisfactory, pressure-tight junction between cooperating portions of a surgical connector.

Still another object of the present invention is to provide apparatus of the nature described which is adapted to permit the user to quickly and easily install a locking ring upon a typical Luer fitting.

A further object of the present invention is to provide a Luer fitting installation apparatus of the character described which includes means for independently supporting cooperating portions of a Luer lock fitting for assembly.

Yet another object of the present invention is to provide a Luer fitting installation tool of the nature described which may be easily manipulated in an environment where time is a critical factor.

A still further object of the present invention is to provide a Luer fitting installation tool which is configured to fit comfortably into the hand of a user for convenient manipulation of the tool.

Another object is to provide apparatus for facilitating connection of an assembled Luer fitting to a portion of flexible tubing or other connector.

These and other objects and advantages of the present invention, along with features of novelty appurtenant thereto, will appear or become apparent in the course of the following descriptive sections.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views:

FIG. 1 is a front elevational view illustrating the best mode of our Luer fitting installation apparatus;

FIG. 2 is a sectional view thereof, taken generally along line 2—2 of FIG. 1;

FIG. 3 is an exploded, isometric view of a typical locking Luer fitting;

FIG. 4 is an isometric view of the jig portion of the present invention;

FIG. 5 is a longitudinal sectional view of the preferred tool body;

FIG. 6 is a front elevational view of the preferred plunger; and,

FIG. 7 is a fragmentary, exploded pictorial view, illustrating the best mode of operation of the tool.

DETAILED DESCRIPTION

With reference now directed to the appended drawings, the installation apparatus of the present invention has been broadly designated by the reference numeral 20. The apparatus 20 comprises a rigid jig, generally designated by the reference number 24, and a hand tool 26 used in conjunction with the jig. Jig 24 may be mounted upon a work table or similar supporting surface 25. Tool 26 is adapted to be conveniently grasped in the hand 29 of a user and manipulated as described hereinafter to facilitate the assembly of a conventional Luer fitting.

With reference now to FIG. 3, a typical Luer fitting has been generally designated by the reference numeral 32. The illustrated fitting may typically be employed in the medical/surgical arts to provide a sterile, leak-proof connection between portions of flexible tubing. Luer fittings may also be conventionally employed in other applications, including pneumatics, hydraulics and the like. Briefly described, a typical Luer fitting 32 comprises a male portion 35, a cooperative female portion 38, and a locking ring portion 42. The male portion 35 comprises an elongated, rigid conduit 46 which terminates at one end in a narrow tip 49 and at the opposite end in a tapered tail 53. Tip 49 is adapted to engage the inner periphery of a length of surgical tubing. The male portion 35 normally includes a geometrically configured key 57.

The female portion 38 of the Luer fitting 32 comprises a rigid cylinder 59 terminating at one end in an integral tip 61 and at the opposite end in an enlarged diameter barrel 65. Tip 1 is adapted to be fitted to a section of flexible surgical tubing. Barrel 65 is adapted to receive the tapered tail 53 of the male portion 35. Barrel 65 terminates at its lower end in a pair of symmetrical, radially spaced-apart flanges 70. Tip 61 and barrel 65 are separated by a rigid shoulder 73 of generally oval configuration. The Luer lock ring 42 is provided to assure a high pressure seal between the male and female Luer fitting components. Locking ring 42 comprises a rigid, generally circular outer shroud 77 terminating at one end in a planar face 81. The outer surface of shroud 77 includes a multiplicity of radially spaced-apart ridges 84 which enable the user to securely grip ring 42. Shroud 77 includes internal threads 83 (FIG. 7) to interfit with flanges 70 of female Luer fitting portion 38 as the latter is screwed into the shroud interior 88. A keyhole 90 is defined centrally within face 81. The geometrical configuration of keyhole 90 facilitates reception and clearance of key 57 of the male portion 35. A sterile, pressure-tight seal is established when the lock ring 42 is properly installed.

As previously implied, apparatus 20 employs a stationary jig 24 to hold the Luer fitting locking ring as the tool installs the male member. As best illustrated in FIGS. 2 and 4, the jig component 24 of apparatus 20 comprises a rigid, generally T-shaped body 92 preferably molded in a durable plastic such as nylon. The planar base 95 includes a pair of mounting orifices 94 adapted to receive appropriate fasteners (not shown) to mount the jig to a suitable supporting surface 25. An integral, generally cubical mounting block 102 extends upwardly perpendicularly from base 95. Block 102 comprises an interiorly defined orifice 115 of a geometrical configuration for matingly receiving shroud 77. As will be readily appreciated, the diameter of orifice 115 must be slightly greater than the diameter of shroud 77. Grooves 118 are radially spaced apart about the orifice 115 for proper registration of shroud 77.

With additional reference now directed to FIGS. 1, 2, and 5, the cylindrical tool 26 includes a rigid, elongated, tubular housing 122. The outer surface of housing 122 is smoothly configured to define a handgrip 125 to comfortably fit into the hand of the user. Handgrip 125 thus facilitates quick and convenient manipulation of the apparatus 20 and prevents the user from quickly tiring and losing a secure grip during use. The handgrip 125 terminates at one end in a smoothly rounded, generally hemispherical head 129. Head 129 is adapted to rest against the base of the user's hand 29, as illustrated in FIG. 7, and thus prevent the hand 29 from slipping off the apparatus 20 during use and interfering with the Luer lock connection process. The opposite end of handgrip 125 comprises a contoured butt 133 which defines an annular opening 136.

A rigid, elongated, nozzle 140 projects outwardly from head 129. In the best mode the tubular nozzle 140 is roughly one half the diameter and one fourth the length of the tool housing 122. The outer periphery of the nozzle is shaped to define an enlarged diameter stop 143 roughly in the center of nozzle. The length of the smaller diameter portion of the nozzle corresponds to the length of shroud 77. The interior 145 of nozzle 140 is of uniform diameter.

As best illustrated in FIG. 5, the interior of tool housing 122 defines a hollow cavity 147 of generally uniform diameter which terminates at its lower end in a concentric shelf 151. Shelf 151 is associated with head 129 and establishes fluid flow communication between the interior 145 of nozzle 140 and cavity 147 of housing 129. A larger diameter ring groove 156 is defined within cavity 147 for captivating a snap ring 194 (FIG. 6). Thus housing 122 is adapted to slidably receive a rigid plunger, generally designated by the reference numeral 160.

With reference now directed to FIGS. 2 and 6, a plunger 160 is adapted to be reciprocally disposed within the housing 122. The plunger preferably comprises a generally hemi-spherical button 164 integral with a rigid, elongated, cylindrical shaft 169. Button 164 is configured to rest comfortably against the thumb or palm of the user's hand 29. Shaft 169 comprises a neck 177 and reduced diameter segments 190 and 184 separated by collar 191. Shaft 169 receives a rigid, metallic drive pin 188 press fitted into shaft segment 184. The steel pin 188 terminates in a blunt end 189. Snap ring 194 is retained upon shaft 169 between neck 177 and collar 191, and it limits longitudinal motion of plunger 160 to prevent it from accidental disassociation from housing 122 (FIG. 2).

An internal spring 197 is coaxially fitted about shaft 169, abutting collar 191. Spring 197 biases the plunger 160 between a loading position and an installation position. When the plunger is depressed, against yieldable spring pressure, pin 188 extends through nozzle 143 to contact the male Luer member 35.

Operation

After jig 24 is properly installed, the mounting orifice 115 faces upwardly toward the user. The locking ring portion 42 of the Luer fitting 32 may then be inserted into block orifice 115, so that its ridges 84 register with grooves 118. When properly positioned, the end of shroud 77 faces upwardly.

The tapered tail 53 of male portion 35 is then slidably inserted into the open end of nozzle 140. Tip 49 and key 57 project from the end of the nozzle. Nozzle 140 is then lowered into the interior 88 of locking ring shroud 77 so that the square key 57 is aligned with the similarly configured keyhole 90. When the user applies a quick impact against button 164 of plunger 160 with his thumb or palm, drive pin 188 contacts the male portion and snap fits it within keyhole 90.

With the assembled half of the fitting 32 securely retained within jig 24, the female portion is then manually screwed into locking ring shroud 77. As the female portion is rotated, flanges 70 contact the tapped interior 88 and its barrel 65 covers tail 53 of the male portion.

Once the fitting is thus tightly assembled, the entire unit may be removed from the jig. Where practical or desirable, the unit may also be retained in the jig to facilitate insertion of the fitting into the end of a portion of flexible tubing or other desired cooperating part, such as a stopcock valve or seal lock.

From the foregoing, it will be seen that this invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. Hand-operated apparatus for assembling and installing a locking Luer fitting of the type comprising a male portion, a female portion, and a threaded locking ring portion, said apparatus comprising:
   hand tool means for forcibly installing said male portion of said fitting, said hand tool means comprising:
      an elongated, tubular body adapted to be grasped in the hand of a user, said tool body comprising an elongated housing having an exterior handgrip and an internal cavity;
      tubular nozzle means projecting outwardly from said body for initially receiving said male portion of said Luer fitting;
      coaxially mounted plunger means slidably disposed within said tool body for forcibly driving said male portion from said nozzle means into said locking ring; and,
      travel limiting means associated with said cavity for restraining movement of said plunger means; and,
   rigid jig means for securing said locking ring portion of said fitting, said jig means comprising base means for mounting said jig means upon a supporting surface and an integral, locking ring-receptive block.

2. The apparatus as defined in claim 1 wherein said travel limiting means comprises an internal ring groove defined within said cavity and a snap ring captivated within said groove and penetrated by said plunger means.

3. The apparatus as defined in claim 2 wherein said plunger means comprises a rigid, elongated shaft operatively associated with a coaxially press-fitted metallic pin.

4. The apparatus as defined in claim 3 including spring means for resiliently yieldably biasing said plunger means toward a tool-load position.

5. Luer fitting assembly apparatus for quick-connection assembly of a Luer lock fitting, said assembly apparatus comprising:
   a rigid, tubular housing having an external handgrip and a hollow internal cavity, said internal cavity comprising a retaining groove;
   rigid, nozzle means integral with said housing for receiving the male portion of said Luer fitting to be assembled;
   rigid, elongated plunger means adapted to be slidably fitted within said internal cavity of said body means for forcibly driving said male portion into the locking ring of said Luer fitting, said plunger means comprising:
   a rigid shaft terminating at one end in a metallic drive pin and at the opposite end in an enlarged diameter button;
   spring means for resiliently biasing said plunger means between a tool-load and an installation position;
   retainer ring means for limiting longitudinal travel of said plunger within said tool, said retaining ring means adapted to be secured with said retaining groove of said internal cavity; and,
   rigid jig means for retaining said locking ring in position for installation, said jig means comprising a planar mounting base and an integral fitting block.

6. A Luer fitting assembly tool adapted to be manipulated by a user to facilitate the assembly of the male portion and locking ring portion of a surgical Luer fitting, said assembly tool comprising:
a rigid, cylindrical body comprising:
a hollow, internal cavity, said internal cavity comprising a shoulder associated with said nozzle means, an opening in said butt portion of said body means, and an internal ring groove;
an external handle comprising a head of a first diameter, a butt portion of equal diameter, and a smaller diameter, intermediate section of bottleneck configuration;
rigid, cylindrical nozzle means integral with said body means for slidably receiving said male portion of said Luer fitting to be assembled by said tool;
rigid, elongated plunger means slidably fitted within said internal cavity of said body for forcibly driving said Luer fitting male portion into engagement with said locking ring of said Luer fitting, said plunger means comprising a rigid shaft terminating at one end in an integral, reduced diameter drive pin and at the opposite end in an enlarged diameter button;
spring means for resiliently biasing said plunger means during operation; and,
retainer ring means captivated within said ring groove for limiting longitudinal travel of said plunger means within said body means.

7. The tool as defined in claim 6 wherein said locking ring portion of said Luer fitting comprises a shroud portion having a plurality of external ridges, and said tool comprises rigid jig means for retaining said locking ring during assembly, said jig means comprising an orifice internally equipped with a plurality of grooves for registering with said shroud ridges.

8. Apparatus for assembling and installing a locking Luer fitting of the type comprising a male portion, a female portion, and a locking ring portion, said apparatus comprising:
hand tool means for forcibly installing said male portion of said fitting, said hand tool means comprising:
an elongated, tubular body adapted to be grasped in the hand of a user, the body defining a hollow interior cavity;
tubular nozzle means projecting outwardly from said body for coupling with said male portion of said Luer fitting;
plunger means slidably mounted within said body for forcibly driving said male portion from said nozzle means into said locking ring portion;
spring means for resiliently yieldably biasing said plunger means in a tool-load position;
means for limiting travel of said plunger means; and,
jig means for securing said locking ring portion of said fitting, said jig means comprising a base for mounting said jig upon a supporting surface, a block portion extending upwardly from said base, and an orifice defined in said block and conformed to fit and receive said locking ring portion.

9. The apparatus as defined in claim 8 wherein locking ring portion comprises a shroud portion having a plurality of external ridges, and said jig means comprises a plurality of grooves defined within said orifice for registering with said ridges.

10. The apparatus as defined in claim 8 wherein said means for limiting travel comprises a ring groove defined within said cavity, and a snap ring captivated within said groove about said plunger means.

11. The apparatus as defined in claim 10 wherein said plunger means comprises an elongated shaft having a neck portion, a collar portion, and a reduced diameter portion between said neck portion and said collar portion penetrating said snap ring, said neck and collar portions adapted to contact said snap ring to restrain shaft movement.

12. The apparatus as defined in claim 11 wherein locking ring portion comprises a shroud portion having a plurality of external ridges, and said jig means comprises a plurality of grooves defined within said orifice for registering with said ridges.

* * * * *